(12) United States Patent
Geithner et al.

(10) Patent No.: US 11,901,152 B2
(45) Date of Patent: Feb. 13, 2024

(54) X-RAY TUBE FOR A STEREOSCOPIC IMAGING

(71) Applicant: Siemens Healthcare GmbH, Erlangen (DE)

(72) Inventors: Peter Geithner, Erlangen (DE); Jörg Freudenberger, Kalchreuth (DE); Christoph Jud, Nuremberg (DE); Anja Fritzler, Erlangen (DE); Josef Deuringer, Herzogenaurach (DE); Peter Hackenschmied, Nuremberg (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 17/874,678

(22) Filed: Jul. 27, 2022

(65) Prior Publication Data

US 2023/0031968 A1     Feb. 2, 2023

(30) Foreign Application Priority Data

Jul. 30, 2021  (EP) ..................... 21188754

(51) Int. Cl.
*H01J 35/06* (2006.01)
*H01J 35/24* (2006.01)
(Continued)

(52) U.S. Cl.
CPC ............ *H01J 35/065* (2013.01); *H01J 35/24* (2013.01); *A61B 6/022* (2013.01); *A61B 6/4007* (2013.01);
(Continued)

(58) Field of Classification Search
CPC ........ H01J 35/065; H01J 35/24; H01J 35/064; H01J 2235/068; A61B 6/022; A61B 6/4007; H05G 1/52
See application file for complete search history.

(56) References Cited

U.S. PATENT DOCUMENTS 4,712,226 A  12/1987  Horbaschek
6,339,635 B1   1/2002  Schardt et al.
(Continued)

FOREIGN PATENT DOCUMENTS

DE   3018541 A1  11/1981
DE   3635948 A1   4/1988
(Continued)

*Primary Examiner* — Chih-Cheng Kao
(74) *Attorney, Agent, or Firm* — Harness, Dickey & Pierce, P.L.C.

(57) ABSTRACT

Some example embodiments provide an x-ray tube for a stereoscopic imaging having an evacuated x-ray tube housing; an electron emitter apparatus in the x-ray tube housing, the electron emitter apparatus including a first field effect emitter with a first emitter surface and a second field effect emitter with a second emitter surface, at least one of the first emitter surface or the second emitter surface being segmented such that a portion of the at least one of the first emitter surface or the second emitter surface can be set relative to the respective overall emitter surface by selectively switching emitter segments of the at least one of the first emitter surface or the second emitter surface; an anode unit in the x-ray tube housing, the anode unit configured to generate x-ray radiation for the stereoscopic imaging as a function of electrons striking two focal points; and a control unit.

20 Claims, 5 Drawing Sheets

(51) Int. Cl.
  *A61B 6/02* (2006.01)
  *A61B 6/00* (2006.01)
  *H05G 1/52* (2006.01)

(52) U.S. Cl.
  CPC ....... *H01J 35/064* (2019.05); *H01J 2235/068* (2013.01); *H05G 1/52* (2013.01)

(56) References Cited

U.S. PATENT DOCUMENTS

| | | |
|---|---|---|
| 8,180,017 B2 | 5/2012 | Forthmann et al. |
| 9,251,992 B2 | 2/2016 | Ishiguro et al. |
| 9,427,198 B2 | 8/2016 | Steinhauser et al. |
| 9,554,757 B2 | 1/2017 | Steinhauser |
| 2010/0040196 A1* | 2/2010 | Zhang ................... A61B 6/504 378/42 |
| 2010/0189221 A1* | 7/2010 | Eaton ....................... G21K 5/02 378/68 |
| 2013/0216021 A1 | 8/2013 | Bernhardt et al. |
| 2015/0043712 A1 | 2/2015 | Wang et al. |
| 2015/0078523 A1 | 3/2015 | Melman |
| 2020/0352531 A1 | 11/2020 | Smith et al. |

FOREIGN PATENT DOCUMENTS

| | | |
|---|---|---|
| DE | 3532822 C2 | 2/1992 |
| DE | 19810346 C1 | 10/1999 |
| DE | 102007027451 A1 | 12/2008 |
| DE | 102011081550 A1 | 10/2013 |
| DE | 202021104081 U1 | 8/2021 |
| EP | 3751593 A1 | 12/2020 |
| WO | WO 2012123843 A1 | 9/2012 |

* cited by examiner

X-RAY TUBE FOR A STEREOSCOPIC IMAGING

CROSS-REFERENCE TO RELATED APPLICATION(S)

The present application claims priority under 35 U.S.C. § 119 to European Patent Application No. 21188754.2, filed Jul. 30, 2021, the entire contents of which are incorporated herein by reference.

FIELD

The invention relates to an x-ray tube for a stereoscopic imaging, a method for generating x-ray radiation for a stereoscopic imaging and an associated computer program product.

BACKGROUND

Objects, in particular patients, to be examined in the medical imaging are three-dimensional. With some applications, recordings are therefore captured from different directions of the patient in order to obtain information about the depth. Such applications in the field of x-ray-based imaging take place for instance in computed tomography devices or in C-arcs during an angiography.

The spatial cognitive ability of the person is routinely not used adequately in these applications. Two x-ray recordings with a small angular offset, which is already described in DE 30 18 541 A1 for instance, are required in order to use this ability. The images reconstructed from these recordings are ideally fed by way of optics to an eye of an observer. As a result, a three-dimensional impression is produced for the observer. Two focal points must be available at a specific distance, preferably at eye distance, for the angular offset of the x-ray recordings.

One possibility is the use of two separate, conventional rotary anodes (see e.g. U.S. Pat. No. 8,180,017 B2, DE 10 2011 081 550 A1 and FIG. 4 in U.S. Pat. No. 9,251,992 B), which may, however, be difficult to realize due to installation size. Stationary anode x-ray tubes according to FIG. 2 in U.S. Pat. No. 9,251,992 B2 require less installation space, but routinely supply too little power, however. A mechanical movement of a single conventional x-ray tube is typically too slow.

A further alternative known from the prior art (WO 2012/123 843 A1, DE 198 10 346 C1, U.S. Pat. No. 9,554,757 B2) is to accommodate two focal points on a single anode in particular by deflecting the electron beam. Here two focal points are present, for instance, on the anode edge of a rotating anode, wherein in this case up to half of the detector can lie in the anode shadow. DE 198 10 346 C1 discloses that a rotation of at least one of the two focal points may be necessary. The situation can be improved by a relatively large but as a result expensive anode. Alternatively, the anode can be tilted, as a result of which in a conventional x-ray tube the x-ray radiation-attenuating focal head lies in the radiation path. EP 3 751 593 A1 discloses in this regard the use of a cathode with an x-ray-transparent material. U.S. Pat. No. 9,554,757 B2 discloses the use of a field effect emitter with nanotubes based on carbon.

DE 36 35 948 A1 describes a beam diaphragm for a stereo image x-ray diagnostics device. DE 35 32 822 A1 discloses a stereo x-ray tube, with which the distance between the focal points is fixed. DE 10 2007 027 451 A1 discloses the use of an x-ray beam splitter by x-ray-optical elements, wherein the known x-ray optics routinely only enable relatively small deflection angles, so that the arrangement described therein is typically technically possible only with large distances between the optics and detector.

SUMMARY

Common to the previously described embodiments is that the usable occupied area of the focal points is relatively small. As a result, the distance between the focal points can typically only be adjusted in a very small range (less than +/−5 mm). The eye distance in humans is on average 65 mm (men) or 62 mm (women), but may vary in the region of between approx. 52 mm and 78 mm depending on physique and size. The embodiments known previously here are not able to adjust the distance between the focal points so that an image optimized to the individual observer is produced. As a result, in some instances the spatial cognitive ability cannot be used despite such x-ray recordings.

One or more example embodiments specify an x-ray tube for a stereoscopic imaging, a method for generating x-ray radiation for a stereoscopic imaging and an associated computer program product, in which the distance between the focal points can be adjusted in a larger range.

One or more example embodiments provide an x-ray tube for a stereoscopic imaging having an evacuated x-ray tube housing; an electron emitter apparatus in the x-ray tube housing, the electron emitter apparatus including a first field effect emitter with a first emitter surface and a second field effect emitter with a second emitter surface, the first emitter surface and the second emitter surface having a substantially x-ray-transparent material, at least one of the first emitter surface or the second emitter surface being segmented such that a portion of the at least one of the first emitter surface or the second emitter surface can be set relative to the respective overall emitter surface by selectively switching emitter segments of the at least one of the first emitter surface or the second emitter surface; an anode unit in the x-ray tube housing, the anode unit configured to generate x-ray radiation for the stereoscopic imaging as a function of electrons striking two focal points; and a control unit, wherein the first emitter surface and the second emitter surface are arranged in a beam path of the x-ray radiation generated in a respective focal point of the two focal points, and the control unit is configured to set a distance between the two focal points by indicating a portion of an electron-emitting surface of at least one of the first emitter surface or the second emitter surface.

According to one or more example embodiments, the substantially x-ray-transparent material is silicon.

According to one or more example embodiments, at least one of the first emitter surface or the second emitter surface form a vacuum-tight housing part of the x-ray tube housing.

According to one or more example embodiments, a focal head of at least one of the first field effect emitter or the second field effect emitter has aluminum.

According to one or more example embodiments, the x-ray tube further includes an interface configured to receive a distance signal which correlates with the distance between the two focal points.

According to one or more example embodiments, the x-ray tube further includes an interface configured to receive an eye movement signal and a further control unit configured to non-axially symmetrically set the portion of the electron-emitting surface as a function of an eye movement signal such that at least one of the two focal points is twisted relative to a grid-shaped segmentation.

According to one or more example embodiments, the anode unit includes a single rotatably mounted disc anode, a region of at least one of the two focal points being in the single rotatably mounted disc anode, the region of at least one of the two focal points has a disc angle of substantially 0°.

According to one or more example embodiments, the anode unit is tilted relative to the first emitter surface and the second emitter surface such that a first plane and a second plane intersect, the first plane including the first emitter surface and the second emitter surface and the second plane including a flat section of the disc anode, the flat section including the two focal points.

According to one or more example embodiments, the anode unit includes a single rotatably mounted roller anode with a cylindrical peripheral surface and the two focal points are arranged axially offset along the cylindrical peripheral surface.

According to one or more example embodiments, the anode unit includes a rotatably mounted disc anode and a further anode, a region of one of the two focal points being in the rotatably mounted disc anode, the region of one of the two focal points has a disc angle of greater than 0°, the two focal points are distributed on the disc anode and the further anode.

According to one or more example embodiments, an axis of rotation of the disc anode is parallel to a plane which comprises the first emitter surface and the second emitter surface.

According to one or more example embodiments, the further anode is a stationary anode or a further rotatably mounted disc anode, a surface of the further anode includes a region of the another focal point, the region of the another focal point has a disc angle of substantially 0°.

According to one or more example embodiments, a method for generating x-ray radiation for a stereoscopic imaging by the x-ray tube includes providing an eye distance of a user of the x-ray tube in the form of the distance signal; transmitting the distance signal to the interface of the x-ray tube; setting the distance between the two focal points; and consecutively generating the x-ray radiation for the stereoscopic imaging in the two focal points.

According to one or more example embodiments, the method further includes obtaining the eye distance from a camera.

According to one or more example embodiments, a non-transitory computer readable medium has instructions which, when executed by a computing unit, cause the computing unit to perform a method according to one or more example embodiments.

BRIEF DESCRIPTION OF THE DRAWINGS

One or more example embodiments of the present invention will be described and explained in more detail with reference to the exemplary embodiments shown in the figures. Basically, substantially constant structures and units will be labeled with the same reference characters as in the case of the first occurrence of the respective structure or unit in the following description of the figures.

In the drawings.

DETAILED DESCRIPTION

Figure 1:
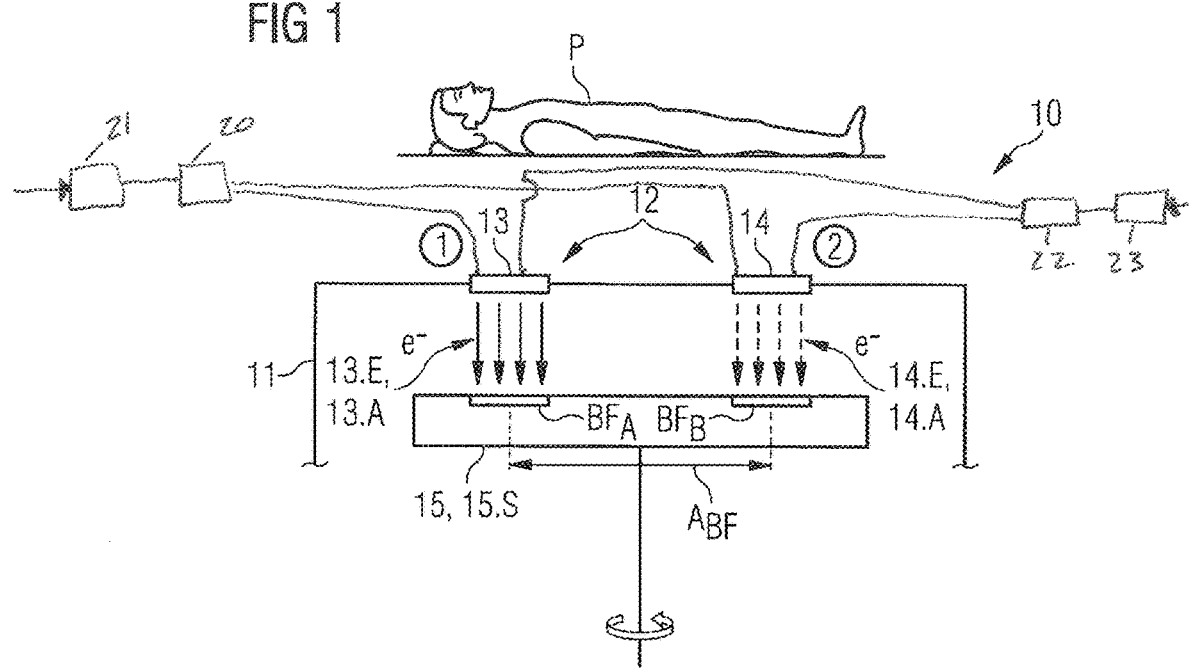
FIGS. 1 to 4 show a first variant of an x-ray tube in different views and developments according to one or more example embodiments.

The inventive x-ray tube for a stereoscopic imaging has
an evacuated x-ray tube housing,
an electron emitter apparatus arranged in the x-ray tube housing,
an anode unit arranged in the x-ray tube housing for generating x-ray radiation for the stereoscopic imaging as a function of electrons striking two focal points and
a control unit,
wherein the electron emitter apparatus comprises a first field effect emitter with a first emitter surface and a second field effect emitter with a second emitter surface,
wherein the first emitter surface and the second emitter surface have an essentially x-ray-transparent material,
wherein the first emitter surface and/or the second emitter surface is segmented so that a portion of the electron-emitting surface can be adjusted relative to the respective overall emitter surface by selectively switching the emitter segments,
characterized in that
the first emitter surface and the second emitter surface are arranged in the beam path of the x-ray radiation generated in the respective focal point and
the control unit is embodied to set a distance between the two focal points by indicating the portion of the electron-emitting surface of the first emitter surface and/or the second emitter surface.

The electron-emitting surface can advantageously be configured arbitrarily so that the distance between the two focal points can be adjusted over a larger range. This is enabled in particular in that the portion of electron-emitting surface can be set flexibly on account of the segmentation of the emitter surfaces. This means in particular that individual segments of the first emitter surface and/or the second emitter surface can be switched on or off, as a result of which the position of the respective electron currents can be varied. Finally, the distance between the two focal points can be influenced only by varying the position of the electron-emitting surface of the first emitter surface or the second emitter surface. The distance across an even larger region can be influenced particularly advantageously if both emitter surfaces are segmented.

The use of the field effect emitter is particularly advantageous because focusing elements and/or deflection units can be routinely omitted on account of their high electron current density. Moreover, the emitter surfaces of such field effect emitters typically have the x-ray-transparent material, so that the x-ray radiation is attenuated comparatively little when the first emitter surface and the second emitter surface are penetrated.

In particular, the x-ray tube is therefore advantageous for such x-ray-based applications in stereoscopic imaging, in which the x-rays are produced consecutively at various focal points and thus at least two recordings are captured from different angles of incidence on the x-ray detector, wherein the two recordings can be shown to a user, thereby producing the spatial impression. These applications can relate in particular to an angiography or computed tomography.

The anode unit comprises at least one anode but may comprise just one single anode depending on the embodiment. The anode is typically mounted rotatably, so that a higher stroke temperature is enabled by the cooling taking place during the rotation and a higher electron current can therefore strike the anode than with a stationary anode. On the rear side, the anode comprises graphite, for instance, for heating the anode surface, which has tungsten and/or molybdenum in the region of the focal point, for instance.

The electrons are accelerated in the direction of the anode unit by the electron emitter apparatus and with the interaction in the two focal points typically consecutively generate the x-ray radiation. The x-ray tube can basically also be embodied to be able to generate x-ray radiation simultaneously in both focal points. The focal points can be part of at least one focal path. The generated x-ray radiation typically has a maximum energy of up to 150 keV as a function of the acceleration voltage applied between the electron emitter apparatus and the anode unit.

An external shape of the first focal point and/or of the second focal point can basically be round but is not routinely round. The outer shape is typically square, for instance rectangular or diamond-shaped. In the radial direction of the anode, the outer shape is typically larger than in the Phi direction, i.e. in the peripheral direction of the anode.

Consecutively (or alternately) means that the generated x-ray radiation can be assigned at a read-out time in each case to a focal point. A frequency of the consecutive x-ray beam generation can be attuned to a read-out frequency of the x-ray detector, which typically integrates the incident photons during a specific time frame, before a recording is generated at a specific read-out time instant. After a first recording at a first read-out time instant with the x-ray radiation of the first focal point, a second recording is routinely captured at a second read-out time instant with the x-ray radiation of the second focal point. This consecutive generation can be repeated arbitrarily, for instance during the entire duration of the imaging examination.

The x-ray tube housing can comprise glass and/or metal. If the first emitter surface and/or the second emitter surface do not form part of the x-ray tube housing, the x-ray tube housing has an x-ray beam exit window in particular there where the radiation path of the x-ray radiation generated in the respective focal point is to leave the x-ray tube housing. The x-ray tube housing is typically surrounded by a cooling medium.

The first field effect emitter and the second field effect emitter are routinely arranged so that a specific distance exists between the first emitter surface and the second emitter surface. The first field effect emitter and the second field effect emitter can basically be arranged so that the first emitter surface and the second emitter surface form a substantially cohesive emitter surface. In this case, a distance between the two emitter surfaces is therefore preferably minimal. Here the first field effect emitter and the second field effect emitter are to be differentiated physically so that each has a separate platform, for instance in the form of a non-cohesive substrate.

Alternatively, the first field effect emitter and the second field effect emitter cannot be differentiated physically but are embodied in an integrated manner on a single platform, so that the electron emitter apparatus has a cohesive emitter surface. In this case, the distinction between the first field effect emitter and the second field effect emitter can take place in that on the software side or electronically this cohesive emitter surface is divided into two adjacently arranged subregions, wherein the first subregion forms the first emitter surface and the second subregion forms the second emitter surface. In this case, it is conceivable for the first emitter surface and the second emitter surface to be newly distributed within the cohesive emitter surface.

It is advantageous if the first emitter surface and the second emitter surface can be compared within the context of a maximum emittable electron current. The segmentation of the two emitter surfaces may be homogeneous which means that they can be subdivided into a number of electron current emission regions of substantially the same high capacity or may be heterogenous. The segmentation can be in the shape of a grid or circular segment. The grid-shaped segmentation can correspond to a pixel-like segmentation with pixels of preferably the same size. It is particularly advantageous if an electrical contacting of the two emission surfaces is preferably configured by the respective field effect emitter so that x-ray-nontransparent materials are largely located outside of the beam path.

The entire emitter surface is predetermined in each case by the first emitter surface or the second emitter surface. The cohesive emitter surface corresponds to the entire emitter surface of the first emitter surface plus the entire emitter surface of the second emitter surface. The electron-emitting surface is defined as that surface from which electrons leave the respective emitter surface and can strike the anode unit in particular without attenuation by a barrier grid. The portion of the electron-emitting surface relative to the respective overall emitter surface can lie between 0%, particularly if at this moment x-ray radiation is generated in the respective other focal point, and 100%, particularly if at another moment in the assigned focal point the x-ray radiation is generated. With x-ray generation the portion is typically less than 100%, for instance in a region between 0.5% and 50%, in particular 2%, so that the electron-emitting surface can be displaced within the respective overall emitter surface with a constant intensity of the electron current.

The electron emission with a field effect emitter is typically effected by the application of a gate voltage, which extracts the electrons from these nanotubes by the electrical field occurring in the tips of the nanotubes, as a result of which the electron current is formed. In addition to switching by the gate voltage, the blockage of a generated electron current can take place by a barrier grid. The selective switching of the emitter segments comprises at least applying the gate voltage and optionally applying a blocking voltage to the barrier grid. The selective switching therefore comprises in particular the switching on and switching off, for instance the applied gate voltage and/or the current limiting units arranged upstream of the nanotubes. Selectively switchable means in particular that each emitter segment can preferably be switched on or off separately. Each emitter segment typically has a plurality of nanotubes. The structure to which the gate voltage typically applies preferably likewise has an x-ray-transparent material, in particular an x-ray-transparent metal, for instance aluminum. The x-ray-transparent material can be a conductive silicon structure, in particular amorphous silicon.

The x-ray tube and/or the electron emitter apparatus can comprise a logic module, in which the control unit and/or a further control unit and/or an interface are integrated. This logic module is used in particular to control the electron emission of the electron emitter apparatus by the first emitter surface and the second emitter surface. The logic module, in particular the control unit, can be embodied to set the portion of the electron-emitting surface relative to the respective overall emitter surface, for instance by the logic module selectively switching the emitter segments. The logic module can be an FPGA module or a processor.

Since the x-ray radiation is typically generated consecutively in the two focal points, the distance relates for instance to the one focal point used just for the x-ray radiation generation, and to the other focal point used previously or to be used subsequently. The distance can be defined for instance by an external boundary line or an intensity gravity point or a geometric center point of the two focal points. In respect of the medically defined eye distance as a distance between the two pupils, the distances specified in the present document relate to the respective geometric center point of the two focal points.

Setting the distance means in particular changing and/or individually regulating the distance. Setting the distance between the two focal points can take place by the control unit in that the portion of the electron-emitting surface of a single emitter surface or both emitter surfaces is set. Indicating the portion of the electron-emitting surface of the first emitter surface and/or the second emitter surface can comprise providing a control signal and/or the selective switching, in other words switching off and/or on of the emitter segments.

The distance can be reduced for instance in that a central emitter segment which lies in a central region between the two focal points is connected, and/or that a decentralized emitter segment which lies outside of the central region between the two focal points is switched off. The connection of the central emitter segment typically does not change a maximum extension of the electron-emitting surface, measured across both focal points. The switching off of the decentralized emitter segment typically reduces the maximum extension of the electron-emitting surface, measured across both focal points.

The fact that the first emitter surface and the second emitter surface are arranged in the beam path of the x-ray radiation generated in the respective focal point means in particular that the usable part of the x-ray radiation at least partially penetrates the respective emitter surface before this can be detected on the x-ray detector. The first emitter surface and the second emitter surface attenuate the x-ray radiation generated on the respective focal point, in particular its usable part, at least minimally, because considered physically the x-ray-transparent material is not 100% transparent. The beam path therefore comprises in particular those x-ray photons, which, under the assumption that no scattering takes place in the x-rayed object, propagate in a straight line from the focal point in the direction of the x-ray detector. Those x-ray photons or the usable part of x-ray radiation are routinely referred to as focal radiation. In other words, the first emitter surface and the second emitter surface are not penetrated exclusively by what is known as extra focal radiation. The extra focal radiation is shielded for instance by the embodiment of the x-ray beam exit window and/or by a collimator and/or by an anti-scatter grid in front of the x-ray detector. The first emitter surface and the second emitter surface are therefore in each case the first object in the beam path, in which what is known as scattered radiation can occur.

One embodiment provides that the x-ray-transparent material is silicon. Silicon field effect emitters are particularly advantageous because on account of a current limiting unit which is to be integrated particularly effectively, these are particularly resistant and thus durable.

One embodiment provides that the first emitter surface and/or the second emitter surface form a vacuum-tight housing part of the x-ray tube housing. This embodiment may mean in particular that the x-ray tube housing in the region of the beam path of the x-ray radiation generated in the respective focal point is penetrated and the emitter surfaces thus inserted in a cut-out can maintain the vacuum of the x-ray tube housing. The penetrated x-ray tube housing and the first emitter surface and/or the second emitter surface can therefore advantageously receive the vacuum within the x-ray tube housing. This results in an advantageously smaller installation size and, on account of the material saving, preferably a lower weight than if the x-ray emitter housing additionally has at least one conventional x-ray radiation exit window.

One embodiment provides that a focal head of the first field effect emitter and/or of the second field effect emitter has aluminum. If the x-ray tube has the focal head, this can consist in particular of aluminum. Aluminum is an x-ray-transparent metal and is thus particularly suited to use in the focal head, which, as part of the electron emitter apparatus, can be disposed at least in part in the beam path of the x-ray radiation. The focal head is then advantageously embodied to be comparatively thin and/or rather parallel to the x-ray radiation.

One embodiment provides that the x-ray tube furthermore has an interface for receiving a distance signal, which correlates with the distance between the focal points. The interface can be in particular part of the control unit or of the logic module. The interface advantageously makes it possible to indicate the distance signal from the outside to the x-ray tube so that the distance between the two focal points can be adjusted individually.

One embodiment provides that the x-ray tube furthermore has a further interface for receiving an eye movement signal and a further control unit for such a non-axially symmetrical setting of the portion of the electron-emitting surface as a function of the eye movement signal so that at least one of the two focal points is rotated relative to the grid-shaped segmentation. The further control unit can be embodied as part of the logic module, similarly to the control unit. The control unit and the further control unit can be mapped in particular using software engineering and/or in a distinguishable manner. The eye movement signal can correlate in particular with an observational axis of the observer or specify this.

One embodiment provides that the anode unit has a single rotatably mounted disc anode, the surface of which in the region of the focal point substantially has a disc angle of 0°, and that the disc anode is thus flat at least in sections. Single means that both focal points are arranged on the same disc anode. The fact that the disc anode is flat means in particular that the disc angle is 0° relative to an axis of rotation section between two circles with different radii and the focal points lie in the region between the two circles. In one particular example, the disc anode is completely flat, wherein the one radius corresponds to the radius of the periphery of the disc anode and the second radius is equal to zero. The advantage of such a flat disc anode is in particular that one of the two focal points or both focal points can be shifted arbitrarily within the flat sections of the disc anode.

One preferred embodiment in respect of the preceding embodiment provides that the anode unit is arranged tilted relative to the first emitter surface and the second emitter surface in such a manner that a first plane, which comprises the first emitter surface and the second emitter surface, and a second plane, which comprises the flat sections with the focal points, intersect one another geometrically. In other words, the first plane and the second plane are not parallel. The definition of the planes is used in particular to clarify the geometric arrangement with one another. This embodiment is particularly advantageous because as a result more electrical power in the form of a higher electron current can be deposited on the disc anode.

An alternative embodiment provides that the anode unit has a single rotatably mounted roller anode with a cylindrical peripheral surface, and that the focal points are arranged axially offset along the peripheral surface. Single means that both focal points are arranged on the same roller anode. The roller anode is advantageous in that a higher power in the form of a higher electron current can be used. This embodiment is in particular advantageous if additionally the further control unit is provided for the non-axially symmetrical setting of the portion of the electron-emitting surface as a function of the eye movement signal.

An alternative embodiment to the preceding embodiments having two anodes provides that the anode unit has a rotatably mounted disc anode, the surface of which in the region of a focal point has a disc angle of greater than 0°, and a further anode, wherein the two focal points are distributed on the disc anode and the further anode. In this embodiment, the position of the one focal point is typically fixed and in particular the position of the other focal point can be changed. The use of the disc anode with the disc angle of greater than 0° preferably enables a relatively high electron beam power in particular also for applications in which no stereoscopic imaging is used, for instance for control scans in order to document medical interventions. This embodiment can advantageously enable an even greater distance between the two focal points.

One embodiment which is preferred to the previous embodiment provides that the disc anode is aligned so that its axis of rotation is parallel to a plane which comprises the first emitter surface and the second emitter surface. This embodiment enables a particularly compact design of an x-ray tube with two anodes in this respect because a distance between the two anodes can be reduced.

One embodiment as a development of one of the two preceding embodiments provides that the further anode is a stationary anode or a rotatably mounted disc anode, the surface of which in the region of the one focal point substantially has a disc angle of 0°, and is thus flat at least in sections. If the stationary anode or the disc anode is flat, the focal point assigned to this anode can shift across a larger region and thus be set more flexibly in accordance with the distance.

The inventive method for generating x-ray radiation for a stereoscopic imaging by an x-ray tube comprises the following steps:
providing an eye distance of a user of the x-ray tube in the form of the distance signal,
transmitting the distance signal to the interface of the x-ray tube
setting the distance between the two focal points and
consecutively generating the x-ray radiation for the stereoscopic imaging in the two distanced focal points.

The user of the x-ray tube is in particular a physician or another correspondingly trained person who uses the x-ray tube during a medical application in order to examine a patient for the stereoscope imaging by x-ray radiation, for instance. The provision can comprise retrieving a value which describes the eye distance from a storage unit or the detection or a manual input of the eye distance. The provision of the eye distance can comprise in particular an eye movement tracking, also referred to as "eye-tracking". In addition to the eye distance, the eye movement can be provided in the form of the eye movement signal. The transmission of the distance signal to the interface of the x-ray tube is typically carried out by a transmit unit, which is connected to the interface by way of a wireless or wired receive unit. The portion of the electron-emitting surface is thereupon set relative to the respective overall emitter surface by selectively switching the emitter segments, as a result of which the distance between the two focal points is set. This distance can be set in particular repeatedly and/or changed repeatedly. After setting the electron-emitting surface, the x-ray radiation for the stereoscopic imaging is generated consecutively in the two distanced focal points.

One embodiment provides that the eye distance is determined by a camera. This embodiment is in particular advantageous because the camera enables a high-frequency and thus rapid detection of the eye distance.

The computer program product can be a computer program or comprise a computer program. The computer program product has in particular the program code means which map the inventive method steps. As a result, the inventive method can be carried out in a defined and repeatable manner and control can be exercised by reproducing the inventive method. The computer program product is preferably configured in such a way that the computing unit can execute the inventive method steps by the computer program product. The program code means can be loaded in particular into a storage device of the computing unit and can typically be executed by a processor of the computing unit with access to the storage device. If the computer program product, in particular the program code means, is executed in the computing unit, typically all inventive embodiments of the described method can be carried out. The computer program product is stored for instance on a physical, computer-readable medium and/or saved digitally as a data packet in a computer network. The computer program product can constitute the physical, computer-readable medium and/or the data packet in the computer network. One or more example embodiments of the present invention can therefore also start from the physical, computer-readable medium, and/or the data packet in the computer network. The physical, computer-readable medium can typically be directly connected to the computing unit, for example in that the physical, computer-readable medium is inserted in a DVD drive or plugged into a USB port, whereby the computing unit can have read access to the physical, computer-readable medium. The data packet can preferably be retrieved from the computer network. The computer network can have the computing unit or be directly connected by a Wide Area Network (WAN) or a (Wireless) Local Area Network connection (WLAN or LAN) to the computing unit. By way of example, the computer program product can be stored digitally on a Cloud server at a storage location of the computer network, be transferred by the WAN via the Internet and/or by the WLAN or LAN to the computing unit in particular by retrieving a download link which points to the storage location of the computer program product.

Features, advantages or alternative embodiments mentioned in the description of the apparatus are likewise to be transferred to the method and vice versa. In other words, claims can be developed for the method with the features of the apparatus and vice versa. In particular, the inventive apparatus can be used in the method.

FIG. 1 shows an x-ray tube 10 for a stereoscopic imaging in a detailed view. The x-ray radiation is used for the examination of a patient P by a user N, not shown.

The x-ray tube 10 has an evacuated x-ray tube housing 11, an electron emitter apparatus 12 arranged in the x-ray tube housing 11 and an anode unit 15 arranged in the x-ray tube housing 11 for generating x-ray radiation for the stereoscopic imaging as a function of electrons striking two focal points BFA, BFB and a control unit 20.

The electron emitter apparatus 12 comprises a first field effect emitter 13 with a first emitter surface 13.A and a second field effect emitter 14 with a second emitter surface 14.A. The first emitter surface 13.A and the second emitter surface 14.A have a substantially x-ray-transparent material. The first emitter surface 13.A and the second emitter surface 13.B are segmented so that a portion of the electron-emitting surface 13.E, 14.E can be set relative to the respective overall emitter surface 13.A, 14.A by selectively switching the emitter segments. The first emitter surface 13.A and the second emitter surface 14.A are arranged in the beam path of the x-ray radiation generated in the respective focal point BFA, BFB and thus between the anode unit 15 and the patient P. The control unit 20 is embodied to set a distance ABF between the two focal points BFA, BFB by indicating the portion of the electron-emitting surface 13.E, 14.E of the first emitter surface 13.A and/or of the second emitter surface 13.B. The propagation direction of the emitted electrons e– is identified with arrows.

In this exemplary embodiment, the first emitter surface 13.A and the second emitter surface 14.A form a vacuum-tight housing part of the x-ray tube housing 11. Moreover, this exemplary embodiment illustrates that the entire emitter surfaces 13.A, 14.A form the electron-emitting surfaces 13.E, 14.E. The distance ABF is defined as a distance between the geometric center points of the two focal points BFA, BFB.

In a particularly advantageous development, the x-ray-transparent material is silicon. In addition, a focal head (not shown) of the first field effect emitter 13 and/or of the second field effect emitter 14 can have aluminum. Moreover, the x-ray tube 10 can have an interface 21 for receiving a distance signal, which correlates with the distance ABF between the focal points BFA, BFB, and/or a further interface 23 for receiving an eye movement signal and a further control unit 22 for setting the portion of the electron-emitting surface 13.E, 14.E in a non-axially symmetrical manner as a function of the eye movement signal, such that at least one of the two focal points BFA, BFB is twisted relative to the grid-shaped segmentation. The control unit 20 and the control unit 22 may be part of a single structure and the interface 21 and the further interface 23 may also be part of a single structure.

The first variant of the x-ray tube 10 is characterized in that the anode unit 15 has a single rotatably mounted disc anode 15.S, the surface of which in the region of the focal point BFA, BFB has substantially a disc angle of 0°, and that the disc anode 15.S is therefore completely flat at least in sections in particular in this exemplary embodiment.

Figure 3:
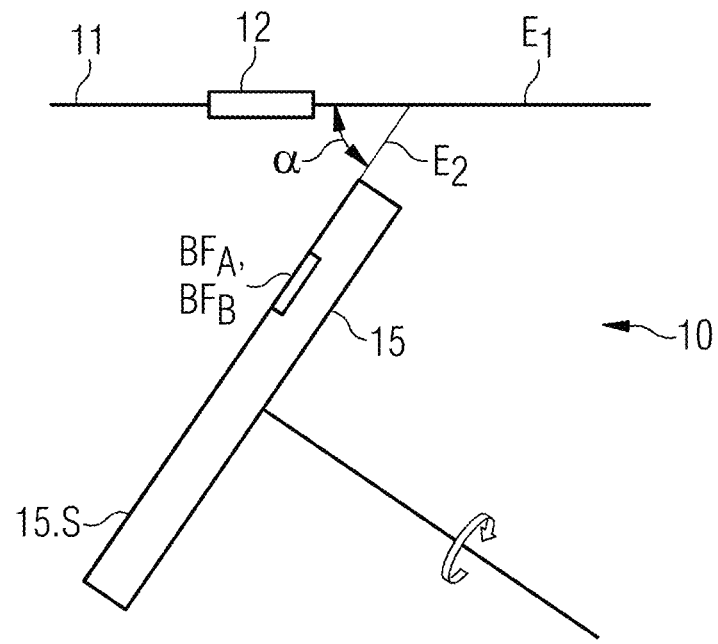

In particular, by comparison with the embodiment in FIG. 3, reference is made to a first plane E1, which comprises the first emitter surface 13.A and the second emitter surface 14.A, and a second plane E2 which comprises the flat sections with the focal points BFA, BFB, therefore not intersecting one another geometrically.

Figure 2:
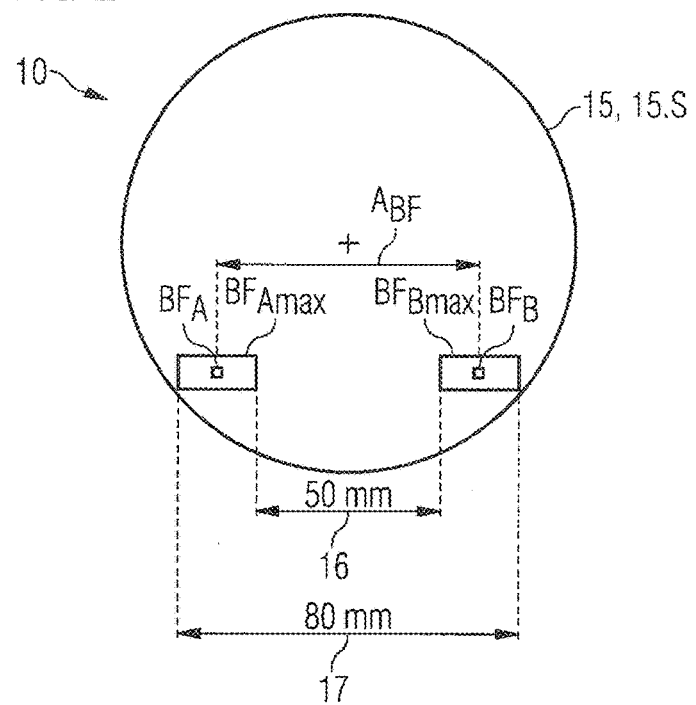

FIG. 2 shows the x-ray tube 10 of the first variant with a top view onto the anode unit 15 from the view of the electron emitter apparatus 12.

The two focal points BFA, BFB are within in each case one maximum focal point surface BFAmax, BFBmax, which represent in particular the region of the surface of the disc anode 15.S in which the focal points BFA, BFB lie, in particular are arbitrarily set, as a function of the portion of the electron-emitting surfaces 13.E, 14.E. By comparison with the exemplary embodiment shown in FIG. 1, for illustrational purposes the portion of the electron-emitting surfaces 13.E, 14.E is smaller than the respective focal point surface BFAmax, BFBmax.

This embodiment typifies a non-cohesive emitter surface, because a focal-point free region 16 is provided between the two maximum focal point surfaces BFAmax, BFBmax. A maximum extension 17 of the electron-emitting surface 13.E, 14.E, measured across both focal points BFA, BFB, is likewise plotted.

FIG. 3 shows the first variant of the x-ray tube 10 according to FIGS. 1 to 2 in an advantageous development.

The anode unit 15 is arranged tilted relative to the first emitter surface 13.A and the second emitter surface 14.A so that a first plane E1, which comprises the first emitter surface 13.A and the second emitter surface 14.A, and a second plane E2, which comprises the flat sections with the focal points BFA, BFB, intersect one another geometrically. The angle at which the two planes E1, E2 intersect, considered mathematically, is identified with a and is greater than 0°. Despite the tilted arrangement a respective distance between the two focal points BFA, BFB and the first emitter surface 13.A and the second emitter surface 14.A is essentially the same.

Figure 4:
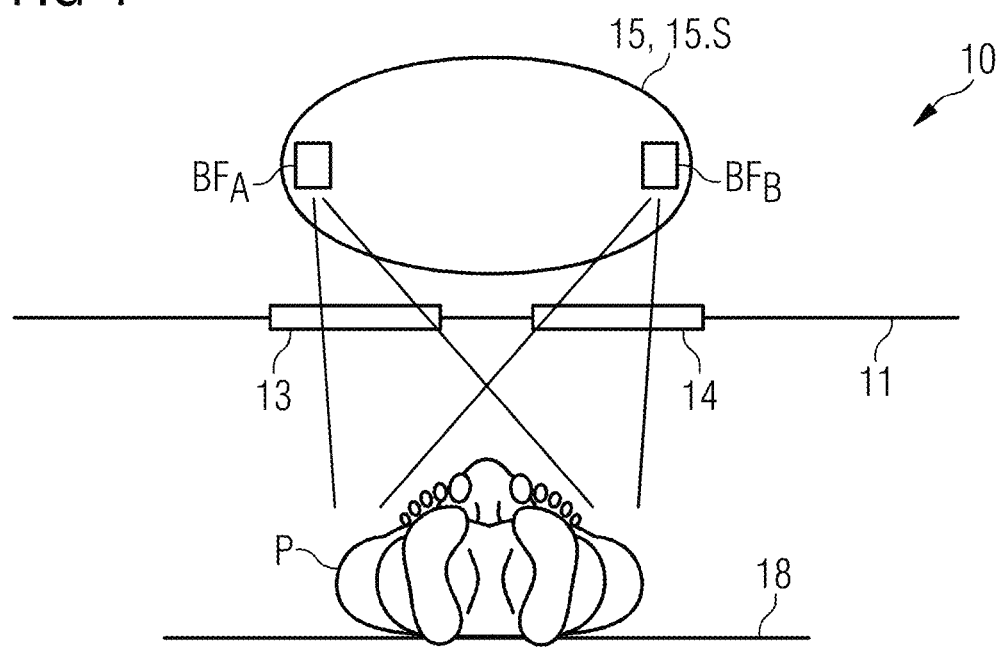

FIG. 4 shows the exemplary embodiment in FIG. 3 in a further schematic view. The x-ray radiation is generated in the two focal points BFA, BFB, wherein the two compartments are to illustrate the beam path of the x-ray radiation, in particular the usable part thereof. The x-ray radiation penetrates the emitter surfaces 13.A, 14.A, thereupon the patient P, arranged in the beam path, and is detectable on the x-ray detector 18.

Figure 5:
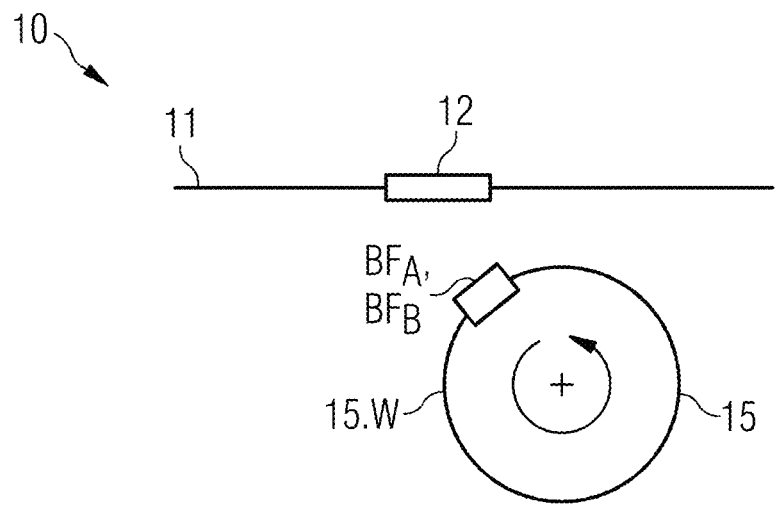
FIGS. 5 to 6 show a second variant of the x-ray tube in different views according to one or more example embodiments.

FIG. 5 shows a second variant of the x-ray tube 10 in a side view.

Compared with the first variant of the x-ray tube 10, the anode unit 15 has a single rotatably mounted roller anode 15.W with a cylindrical peripheral surface.

Figure 6:
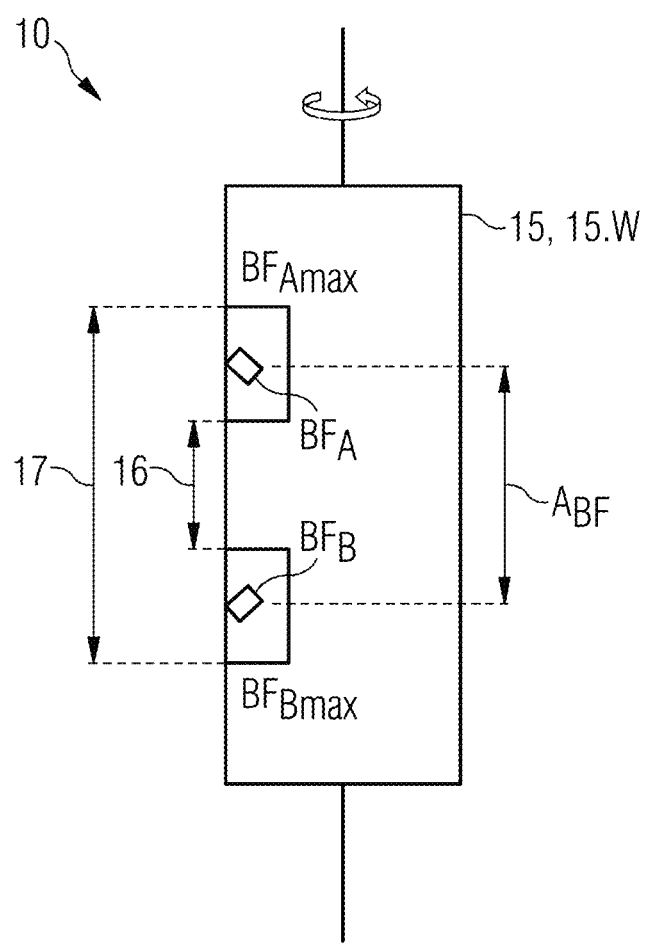

FIG. 6 shows a top view of the second variant of the x-ray tube 10 according to FIG. 5. The focal points BFA, BFB are arranged axially offset along the peripheral surface. In this exemplary embodiment, the effect can be reproduced by way of example if the portion of the electron-emitting surface 13.E, 14.E is set to be non-axially symmetrical as a function of the eye movement signal so that both focal points BFA, BFB, in particular their outer shape, is rotated relative to the grid-shaped segmentation.

Figure 7:
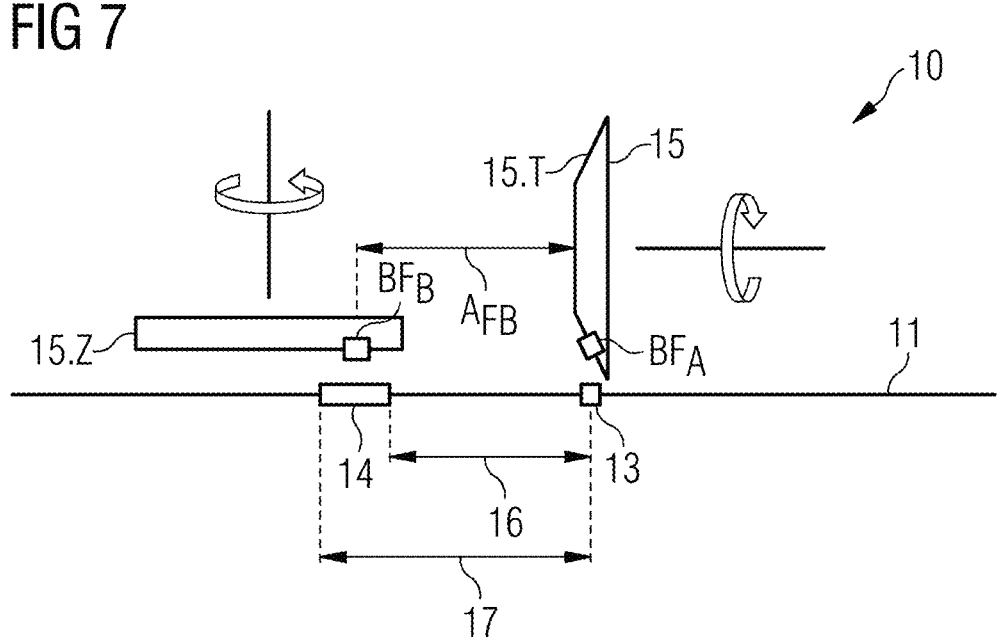
FIGS. 7 to 8 show a third variant of the x-ray tube in different views according to one or more example embodiments.

FIG. 7 shows a third variant of the x-ray tube 10 in a side view.

By comparison with the first and second variant of the x-ray tube 10, the anode unit 15 has a rotatably mounted disc anode 15.T, the surface of which in the region of a focal point BFB has a disc angle of greater than 0°, and a further anode 15.Z, wherein the two focal points BFA, BFB are distributed on the disc anode 15.T and the further anode 15.Z.

The disc anode 15.T is aligned so that its axis of rotation is parallel to a plane, which comprises the first emitter surface 13.A and the second emitter surface 14.A. Alternatively, the axis of rotation could be rotated up to and including 90° so that this axis of rotation is parallel to the axis of rotation of the rotatably mounted disk anode.

In this exemplary embodiment, the further anode 15.Z is a rotatably mounted disc anode, the surface of which in the region of the one focal point BFB substantially has a disc angle of 0°, and is thus flat at least in sections. Alternatively, the further anode 15.Z can be a stationary anode.

Figure 8:
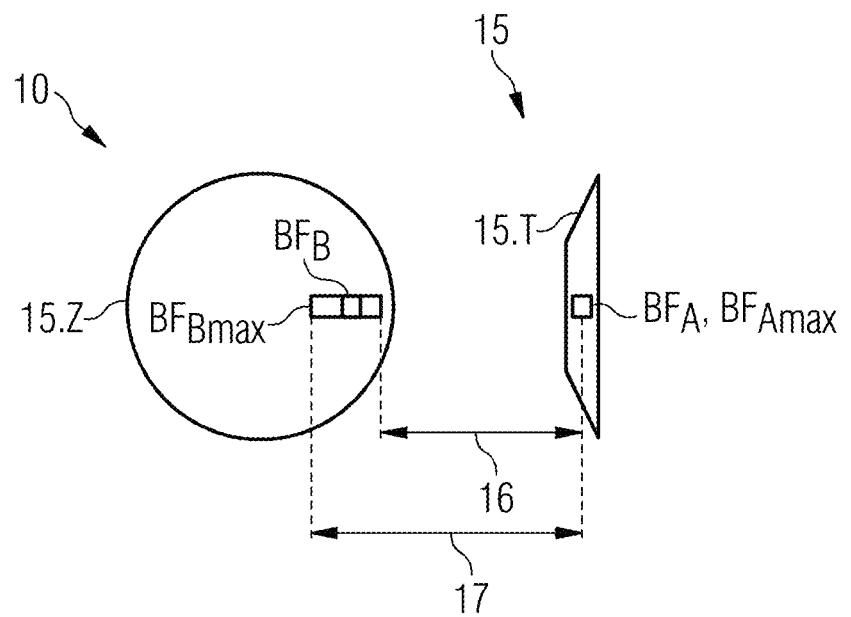

FIG. 8 shows a top view of the third variant of the x-ray tube 10.

This figure shows that the focal point BFA corresponds to the maximum focal point surface BFAmax because the position of the focal point BFA in the direction of the focal point BFB is essentially unchangeable. In this embodiment, the intensity of the electron current, which may have an influence on the outer shape of the focal point BFA within the limits of the maximum focal point surface BFAmax, is typically variable.

Figure 9:
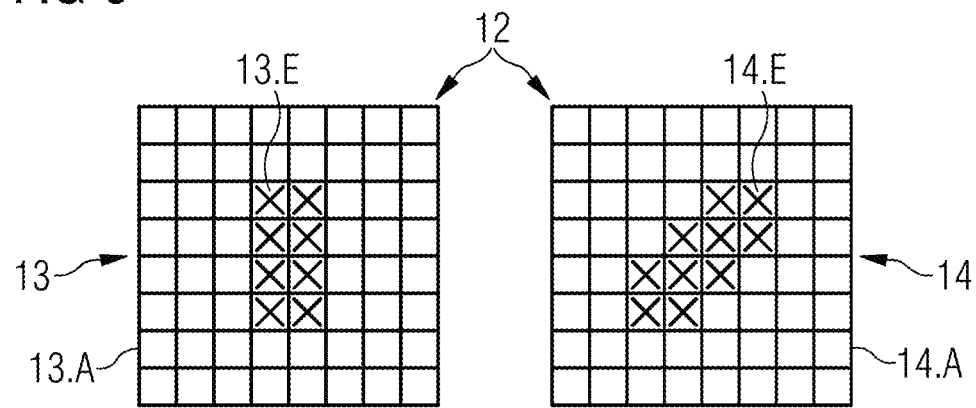
FIG. 9 shows an electron emitter apparatus according to one or more example embodiments.

FIG. 9 shows an electron emitter apparatus 12 in a detailed view, which can be provided in each of the three shown variants of the x-ray tube. The electron emitter apparatus 12 has the first field effect emitter 13 and the second field effect emitter 14, which have no cohesive emitter surface. The two field effect emitters 13, 14 are therefore separated physically.

The first emitter surface 13.A and the second emitter surface 14.A are each segmented in a grid-shaped manner in an 8×8 matrix. It is basically conceivable for the number of rows to differ from the number of columns. The number of rows or columns can amount to more than 8, in particular 256, 512, 1024 or more, for instance.

The exemplary embodiment in FIG. 9 shows in each case the portion of the electron-emitting surface 13.E, 14.E, by the respective electron-emitting and thus switched-on segments being identified with an X. The switched-off segments not identified with X do not emit electrons.

The portion of the electron-emitting surface 14.E is, for instance as a function of the eye movement signal, set in a non-axially symmetrical manner so that the focal point BFA, BFB resulting therefrom is twisted relative to the grid-shaped segmentation.

Figure 10:
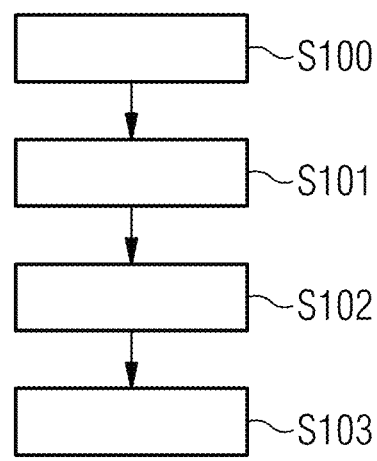
FIG. 10 shows a method for generating x-ray radiation for a stereoscopic imaging by an x-ray tube according to one or more example embodiments.

FIG. 10 shows a method for generating x-ray radiation for a stereoscopic imaging by an x-ray tube 10 in a flow chart.

Method step S100 identifies a provision of an eye distance of a user of the x-ray tube 10 in the form of the distance signal. Before provision the eye distance can be determined for instance by a camera.

Method step S101 identifies a transmission of the distance signal to the interface of the x-ray tube 10.

Method step S102 identifies a setting of the distance between the two focal points, in particular in the control unit of the x-ray tube 10.

Method step S103 identifies a consecutive generation of the x-ray radiation for the stereoscopic imaging in the two distanced focal points.

Although some example embodiments of the present invention have been disclosed in the form of preferred embodiments and variations thereon, it will be understood that numerous additional modifications and variations could be made thereto without departing from the scope of example embodiments of the present invention. For the sake of clarity, it is to be understood that the use of "a" or "an" throughout this application does not exclude a plurality, and "comprising" does not exclude other steps or elements. The mention of a "unit", "module" or a "device" does not preclude the use of more than one unit or device.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module', 'unit', 'interface' or the term 'controller' may be replaced with the term 'circuit.' The term 'module' and 'unit' may refer to, be part of, or include hardware, e.g., processor hardware (shared, dedicated, or group) that executes code and memory hardware (shared, dedicated, or group) that stores code executed by the processor hardware.

The module or interface may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion.

In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices (i.e., storage means). The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Although some example embodiments of the present invention have been illustrated and described in detail by the preferred exemplary embodiments, the invention is nevertheless not restricted by the examples given and other variations can be derived therefrom by the person skilled in the art without departing from the protective scope of the invention.

The invention claimed is:

1. An x-ray tube for a stereoscopic imaging, comprising:
an evacuated x-ray tube housing;
an electron emitter apparatus in the x-ray tube housing,
  the electron emitter apparatus including a first field effect emitter with a first emitter surface and a second field effect emitter with a second emitter surface,
  the first emitter surface and the second emitter surface having a substantially x-ray-transparent material,
  at least one of the first emitter surface or the second emitter surface being segmented such that a portion of an electron-emitting surface can be set relative to the first emitter surface and the second emitter surface by selectively switching emitter segments of at least one of the first emitter surface or the second emitter surface;
an anode unit in the x-ray tube housing, the anode unit configured to generate x-ray radiation for the stereoscopic imaging as a function of electrons striking two focal points; and
a control unit, wherein
the first emitter surface and the second emitter surface are arranged in a beam path of the x-ray radiation generated in respective focal points of the two focal points, and the control unit is configured to set a distance between the two focal points by indicating the portion of the electron-emitting surface of at least one of the first emitter surface or the second emitter surface.

2. The x-ray tube as claimed in claim 1, wherein the substantially x-ray-transparent material is silicon.

3. The x-ray tube as claimed in claim 1, wherein at least one of the first emitter surface or the second emitter surface form a vacuum-tight housing part of the x-ray tube housing.

4. The x-ray tube as claimed in claim 1, wherein a focal head of at least one of the first field effect emitter or the second field effect emitter has aluminum.

5. The x-ray tube as claimed in claim 1, further comprising:
an interface configured to receive a distance signal which correlates with the distance between the two focal points.

6. The x-ray tube as claimed in claim 1, further comprising: an interface configured to receive an eye movement signal and a further control unit configured to non-axially symmetrically set the portion of the electron-emitting surface as a function of an eye movement signal such that at least one of the two focal points is twisted relative to a grid-shaped segmentation.

7. The x-ray tube as claimed in claim 1, wherein the anode unit includes a single rotatably mounted disc anode, a region of at least one of the two focal points being in the single rotatably mounted disc anode, the region of at least one of the two focal points has a disc angle of substantially 0°.

8. The x-ray tube as claimed in claim 7, wherein the anode unit is tilted relative to the first emitter surface and the second emitter surface such that a first plane and a second plane intersect, the first plane including the first emitter surface and the second emitter surface and the second plane including a flat section of the disc anode, the flat section including the two focal points.

9. The x-ray tube as claimed in claim 1, wherein the anode unit includes a single rotatably mounted roller anode with a cylindrical peripheral surface and the two focal points are arranged axially offset along the cylindrical peripheral surface.

10. The x-ray tube as claimed in claim 1, wherein the anode unit includes a rotatably mounted disc anode and a further anode, a region of one of the two focal points being in the rotatably mounted disc anode, the region of one of the two focal points has a disc angle of greater than 0°, and the two focal points are distributed on the disc anode and the further anode.

11. The x-ray tube as claimed in claim 10, wherein an axis of rotation of the disc anode is parallel to a plane which comprises the first emitter surface and the second emitter surface.

12. The x-ray tube as claimed in claim 10, wherein the further anode is a stationary anode or a further rotatably mounted disc anode, a surface of the further anode includes a region of the another focal point, the region of the another focal point has a disc angle of substantially 0°.

13. A method for generating x-ray radiation for a stereoscopic imaging by the x-ray tube as claimed in claim 5, the method comprising:
providing an eye distance of a user of the x-ray tube in the form of the distance signal;
transmitting the distance signal to the interface of the x-ray tube;
setting the distance between the two focal points; and
consecutively generating the x-ray radiation for the stereoscopic imaging in the two focal points.

14. The method as claimed in claim 13, further comprising:
obtaining the eye distance from a camera.

15. A non-transitory computer readable medium having instructions which, when executed by a computing unit, cause the computing unit to perform the method as claimed in claim 13.

16. The x-ray tube as claimed in claim 2, wherein at least one of the first emitter surface or the second emitter surface form a vacuum-tight housing part of the x-ray tube housing.

17. The x-ray tube as claimed in claim 2, wherein a focal head of at least one of the first field effect emitter or the second field effect emitter has aluminum.

18. The x-ray tube as claimed in claim 3, wherein a focal head of at least one of the first field effect emitter or the second field effect emitter has aluminum.

19. The x-ray tube as claimed in claim 2, further comprising:
an interface configured to receive a distance signal which correlates with the distance between the two focal points.

20. The x-ray tube as claimed in claim 3, further comprising:
an interface configured to receive a distance signal which correlates with the distance between the two focal points.

* * * * *